Figure 1:
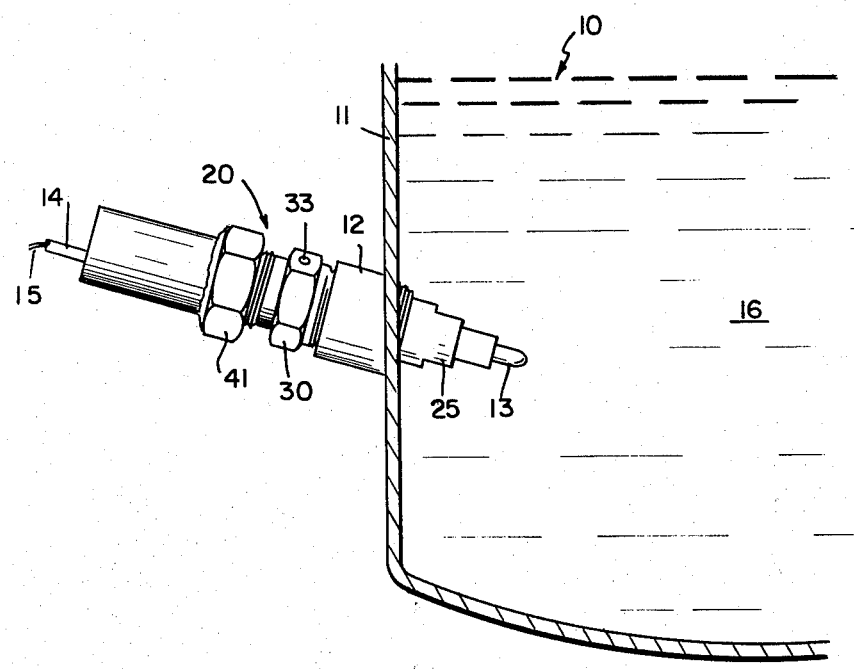

United States Patent [19]

Sheets

[11] 4,315,990
[45] Feb. 16, 1982

[54] FERMENTATION SYSTEM AND PROBE DETECTOR HOLDER

[75] Inventor: Francis E. Sheets, Indianapolis, Ind.

[73] Assignee: Eli Lilly and Company, Indianapolis, Ind.

[21] Appl. No.: 158,498

[22] Filed: Jun. 11, 1980

[51] Int. Cl.³ .............................................. C12M 1/34
[52] U.S. Cl. .................................. 435/291; 435/287; 435/289; 435/290
[58] Field of Search .................. 435/3, 287, 289, 290, 435/291, 313, 314, 315, 316, 317, 807, 808, 817

[56] References Cited

U.S. PATENT DOCUMENTS 3,954,565  5/1976  Boiko et al. .................. 435/291 X
4,021,120  5/1977  Muller et al. .................. 435/808 X

OTHER PUBLICATIONS

Dr. Ingold, Specification E 764-31B/70, 1963 Zurich, Switzerland, p. 2096, distributed by Chemapec, Inc., Hoboken, New Jersey.
Dr. Ingold, E-764-20 Pressurized Straight Flow Assembly Unit 764-20/764-31, distributed by Chemapec, Inc., Hoboken, New Jersey.
Dr. W. Ingold, "Pressurized Elbow Flow Assembly Unit" 712-11/764-32.
Dr. Ingold, E764-INF "Industrial pH Measurement Using Pressurized Immersion Assemblies," distributed by Chemapec, Inc., Hoboken, New Jersey, pp. 1-2.
"Ingold Threaded Nipples, Blind Plugs and Protector Shields," distributed by Chemapec, Inc., Hoboken, New Jersey, pp. 1-5.

Arthur H. Thomas Company, *Scientific Apparatus and Reagents*, Nov. 1968, vol. 5, No. 1, pp. 1-4.

*Primary Examiner*—Robert J. Warden
*Attorney, Agent, or Firm*—Jenkins, Coffey, Hyland, Badger & Conard

[57] ABSTRACT

A system for the preparation of biological agents can include a vessel in which the biological agents are fermented and in which the fermentation is monitored by a probe detection means. Probe support means are fastened to the wall of the vessel to support the probe detection means with its operative end within the vessel and to provide access from outside the vessel to the output of the probe detection means. The probe support means has a seal-engaging surface at its forwardmost end within the tank. A seal is seated on the probe detection means forwardly of probe support means, and a seal compression member is fastened to the probe support means to compress the seal between the seal-engaging surface of the probe support means, the seal compression means, and the outer surface of the probe detection means to limit the collection of fermentation material to the exposed outer surfaces of the system and permit cleansing and sterilization of the system. In addition, the probe support means can receive a second seal rearwardly of the surface to which the seal compression member is fastened. The seal compression member and the probe support means are adapted so that the end of the seal compression member can also compress the second seal between the probe support means and the end of the seal compression member.

9 Claims, 2 Drawing Figures

FERMENTATION SYSTEM AND PROBE DETECTOR HOLDER

This invention relates to an improved system for the preparation of biological agents and permits more complete cleansing and sterilization of a fermentation system upon the completion of manufacture of one batch of materials, thereby precluding contamination of a second batch of materials.

A number of biological agents are prepared by processes involving fermentation and must be manufactured in batches. Examples include such materials as penicillin and tylosin, a Lilly agricultural product for the medication of respiratory diseases in chickens. Such biological agents are most commonly prepared by processes in which materials are fermented in large tanks. The fermentation processes must be closely controlled and the systems used in these processes include detection means or probe electrodes which extend into the materials being fermented within the tank to permit monitoring of the fermentation process.

Probe detector means may include pH and dissolved oxygen electrodes, ionic-type probes, and enzymatic probes. During the preparation of a batch of biological agents, such probe detection means may be used to monitor the process. Upon the completion of the preparation of one batch of agents or pharmaceuticals, it is necessary to sterilize the system in which they were prepared in order that a new batch may be prepared without contamination. Spores and bacteria that may remain from a completed batch, if not killed and removed from the system, can grow and contaminate a subsequent batch.

The systems known before this invention included recesses, where the probe detection means entered the fermentation tank, that became contaminated with spores and bacteria and that were difficult to cleanse and sterilize. In some such systems, a seal, such as an O-ring, was provided at the inner bore of the probe detector support means near its end within the fermentation tank. Such O-ring seals were carried within an O-ring groove located a fraction of an inch inwardly from its end. These prior systems relied upon the slight compression of the O-ring seal between the outer surface of the electrode and the bottom of the O-ring groove. The seal did not satisfactorily preclude and seal against the collection of bacteria and spores in the system, and it included recesses between the forwardmost end of the probe detector support means and the electrode and between the O-ring groove and the O-ring and provided significant collection sites for spores and bacteria which could not be satisfactorily cleansed and sterilized.

The system of this invention has no significant sites in which spores and bacteria may collect that may not be cleansed and sterilized and provides sealed probe detection means that precludes fermentation materials from bypassing the seal and substantially eliminates any recesses that are exposed to the fermentation materials. In the system, the probe detector carries a seal seated on the probe detector outer surface forwardly of the probe detector support means. A seal compression member is fastened to the forward surface of the probe detector support means in such a manner that the seal is compressed between the forwardmost surface of the probe detector support means, the outer surface of the probe, and the seal compression member, to seal the system and substantially eliminate recesses.

In a preferred embodiment, the seal compression member is threaded onto a cylindrical surface of a probe detector support means; and the probe detector support means has a concave, frustoconical, seal-engaging surface at its forwardmost portion to cooperate with a concave, frustoconical, seal-engaging surface within the seal compression member to form, when the two are threadedly engaged, a V-shaped cavity into which the seal is compressed as the seal compression member is threaded onto the probe detector support means. The seal is thus compressed between the two members and urged outwardly of the V-shaped cavity to the annular gap between the outer surface of the probe and the seal compression member. In addition, the exposed outer face of the seal compression member may be provided with a concave, frustoconical surface to reduce the length of, or substantially eliminate, the annular gap between the outer surface of the probe detector and the seal compression member.

In addition, the system may include a second seal carried by the probe detector support means rearwardly of the surface engaged by the seal compression member. The seal compression member and the forwardmost portion of the probe detector support means are adapted so that the second seal is compressed between the distal end of the seal compression member and an adjacent surface portion of the probe detector support means as the seal compression member compresses the first seal.

Thus, a system of the invention may include a tank or conduit, or other such vessel in which biological agents are produced with fittings in the wall of the vessel for the insertion of probe detection means to monitor the process. Probe detection means may be ionic or enzymatic probes or electrodes for the determination of pH and dissolved oxygen or other such process parameter monitors. A probe support means adapted to be fastened to the vessel wall includes an inner bore adapted to receive the probe detection means. When in place in the system, the probe support means carries the probe detection means in such a manner that the operative end of the probe detection means extends from the probe support means within the vessel. The portion of the probe support means extending within the vessel may have a threaded cylindrical end and a seal-engaging surface adjacent the projecting probe. A compressible seal or gasket, such as an O-ring, may be placed about the outer surface of the probe detection means; and a seal compression member can be placed about the probe and threaded onto the probe support means to compress the seal between it, the seal-engaging surface of the probe support means and the outer surface of the probe detection means. In such a system, the probe detection means is sealed and an annular gap between the outer surface of the probe and the seal compression member can be precluded.

The probe support means may also include a grommet-seating surface at the end of the inner bore which lies outside of the vessel wall. Surrounding the grommet-seating surface outside of the tank wall will be a second threaded outer surface. A grommet can be placed surrounding the probe detection means so that when it is placed within the probe support means, the grommet rests upon the grommet-seating surface, and a grommet compression nut may be threaded onto the second threaded outer surface of the probe support means to compress the grommet between the grommet-seating surface of the probe support means and the probe itself, thereby supporting the probe within the probe support means.

Figure 2:
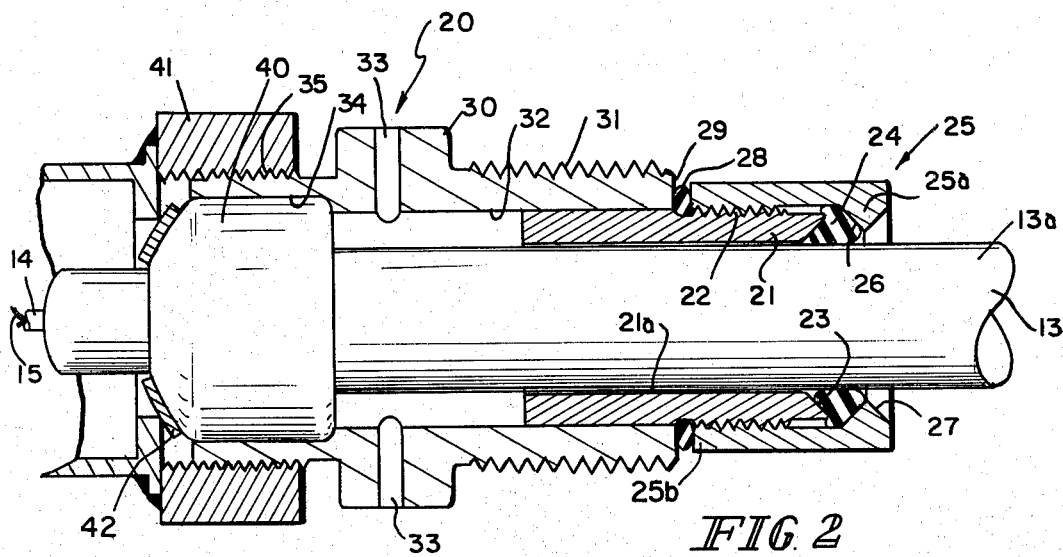

Further features and advantages of this invention will be apparent from the following description and drawings in which:

FIG. 1 is a partial cross-sectional view of a system of this invention taken through the wall of a fermentation tank and showing the probe detection means and probe support means; and FIG. 2 is a partial cross-sectional view of the probe detector support means at a plane through its central axis and showing the manner of its support and sealing engagement with a probe electrode means.

A system of this invention is illustrated in FIG. 1. Such a system includes a vessel, such as tank 10 formed by a tank wall 11 to contain a biological agent 16 which is subjected to processing as, for example, by fermentation. The process, as experienced by the biological agent 16, is monitored by the operative end of a probe detection means 13 within the tank. The probe detection means 13 may be any means to detect or monitor parameters of the process within the tank. Examples of such probe detection means may be electrodes for monitoring the pH and the dissolved oxygen content of material 16 within the tank as it is being processed. The probe 13 is supported in a fitting 12 in the wall 11 of a tank by a probe detector, or electrode, support means 20. The probe detector support means 20 supports the detector 13 so that its operative end is exposed to the material 16 being processed within the tank and the probe output means 14 extends outwardly of the tank to permit the signal from the detector, for example on wires 15, to be monitored. Although the operation of a probe detection means is frequently monitored by means of an electrical signal imposed upon conductors leading to the operative portion of an electrode, monitoring of the contents of the tank and the advantages of this invention are not limited to electrodes that are so monitored.

FIG. 2 shows the probe detector holder of this invention in substantially greater detail through a cross-sectional view of the probe support means 20, and the elements associated therewith, taken along a plane through their central axes. The detector 13 is not shown in cross section in FIG. 2 to avoid unnecessary detail.

As shown in FIG. 2, the probe support means 20 can have a cylindrical inner member 21 having an inner bore 21a adapted to receive the detector and a threaded outer surface 22. At the end of the probe support means 20 within the tank, is a seal-engaging surface 23, shown in FIG. 2 as a concave, frustoconical, seal-engaging surface formed in the forwardmost end of the inner member 21. A seal 24 is placed over the outer surface 13a of the detector 13 just forwardly of the probe support means 20. A seal compression member 25, such as the special flanged nut shown in FIG. 2, is threaded onto the outer surface 22 of the probe support means 20, thereby compressing the seal 24 between seal compression member 25, the forwardmost seal-engaging surface 23 of the probe support member 20 and the outer surface 13a of the detector 13. In its preferred embodiment, the seal compression member 25 is provided with an annular flange 25a having an inner seal-engaging surface 26 and an outer annular gap-precluding surface 27. As shown, the annular flange 25a has a concave, frustoconical, seal-engaging suface 26 within the annular flange 25a and a concave, frustoconical surface 27 on the outside surface of the annular flange 25a to provide a line intersection between the surfaces 26 and 27 so that, upon compression of the seal, it may be urged to the annular gap between seal compression member 25 and the outer surface of the probe 13, thereby sealing the forward portion of the probe support means and substantially eliminating any recess that may be difficult to clean and sterilize.

In addition to the first seal 24, a second seal 28 may be carried by the probe support means 20 rearwardly of the threaded surface 22; and probe support means 20 may be provided with an extending surface, or boss 29. Seal compression member 25, the forwardmost inner portion 21 of probe support means, and its threaded outer surface 22 may be adapted so that, as the seal compression means 25 is threaded onto the inner portion 21 of the probe support means 20, the second seal 28 is compressed between the distal end 25b of the seal compression member 25 and the boss-like surface 29 of the probe support means, thereby compressing the second seal 28 to substantially preclude the formation of a recess between the seal compression member 25 and the probe support means 20.

The probe support means 20 may also include a housing 30 which is preferably provided with a threaded outer surface 31 adapted to be threaded into the fitting 12 in tank wall 11. As shown in FIG. 2, the inner member, or portion 21, of the probe support means 20 extending within the vessel may be a separate, cylindrical member that is pressed into and welded to the housing 30; however, the housing 30 and inner portion 21 may be machined from a single piece of material. Where housing 30 and the inner member 21 are separate pieces, the second seal 28 is located to preclude fermentation material from penetrating their interface.

The housing 30 has a housing inner bore 32 and can be provided with an opening 33 to permit the escape of fermentation material reaching the housing inner bore 32 and the detection of the failure of the system. The outer end of the housing inner bore 32 may be provided with a grommet-seating surface 34, and the housing may be provided with a second threaded outer surface 35 surrounding the grommet-seating surface 34. With this arrangement, the detector 13 may be inserted within a grommet 40 before it is placed within the probe support means 20. A grommet compression nut 41 may be threaded onto the second threaded outer surface 35 of the housing 30 to compress the grommet 40 against the grommet-seating surface 34 and outer surface of the detector 13, thereby supporting the probe 13 within the probe support means 21. A washer 42 may be provided between the grommet 40 and the grommet compression nut 41 to more evenly apply pressure to the grommet 40. The grommet compression nut 41 shown in FIG. 1 and FIG. 2 is intended for use with pH electrodes. Other members may be fitted to the probe support means 20 by the second threaded outer surface to accommodate dissolved oxygen electrodes or other types of probes.

A typical detector support for such a system can be made from stainless steel 316. The housing 30 can be turned from stainless steel 316 hexagonal bar stock of a sufficiently large and convenient size. The inner member 21 may be turned from cylindrical stainless steel bar stock to an outside diameter of about 0.687 inch and a length of about one inch. The inner bore 21a can have a diameter, for example, of 0.484 inch to receive a pH and dissolved oxygen electrode. The outer surface 22 may be provided with 11/16-20 threads located on the forwardmost half of its length. The threaded portion 22 can have a length of 5/16 of an inch beginning ⅛ of an inch from the end of the inner member 21. The inner member 21 may be pressed ½ inch into housing 30 and welded to provide a unitary probe support means 20. The forwardmost face of the inner member 21 can be provided with a frustoconical, seal-engaging surface 23 cut at an included angle of about 45° with respect to its central axis. The assembly of the inner member 21 with housing 30 can form an extended surface or boss 29 at the forwardmost surface of the housing 30. The seal compression member 25 is also made from stainless steel 316. It can be turned from round stock about ⅞ of an inch in diameter and provided with "flats" to permit the use of tools such as a wrench. The seal compression member 25 is provided with a central opening of 0.484 inch to permit it to be placed over a detector such as a pH and dissolved oxygen electrode. The seal compression member is also bored and threaded to provide 11/16-20 threads to mate the outer threaded portion 22 of the inner member 21. An annular flange 25a is formed at the forward portion of the seal compression member. The inner face 26 of the annular flange is turned at an included angle of about 45° with respect to its central axis to provide a concave, frustoconical, seal-engaging surface within the seal compression member and to form with the seal-engaging surface 23 of the inner member 21 a V-shaped cavity for the seal when the seal compression member 25 is threaded onto the inner member 21. In addition, the outer face of the annular flange 25a is turned at an included angle of about 30° with respect to its central axis to form a concave, frustoconical outer surface 27 that intersects the frustoconical inner surface 26 of the annular flange in, generally, a circular line thereby substantially eliminating any annular recess when the seal compression member 25 and the inner member 21 are assembled with a probe electrode. The length of the seal compression member is ½ inch so that its distal end 25b will lie closely adjacent the extended boss surface 29 of housing 30 when it is seated on the inner member 21. A second seal 28 placed rearwardly of the threaded outer surface 22 of the inner portion 21 adjacent the surface 29 of the probe support means 20 can thus be compressed between the seal compression member 25 and the surface 29.

Thus, in the system of the invention, probe detection means may be supported with its operative end exposed to a biological agent within a tank or conduit. Such systems may be useful not only in the production of pharmaceutical materials, but also in the commercial fermentation of yeast and in waste treatment systems. The system provides seals which are compressed to seal the system and prevent the escape of the biological agent and preclude recesses in which spores and bacteria may accumulate, and to provide a system that can be easily cleansed and sterilized between batches of materials.

While I have shown and described specific embodiments of the system of this invention, other embodiments may be devised without departing from the scope of the invention as set forth in the following claims.

What is claimed is:

1. A system for the preparation of biological agents, comprising
   a tank for the fermentation of biological agents;
   a threaded fitting in the tank wall;
   a detector to monitor the fermentation process;
   detector support means threadedly engaging the threaded fitting in the tank wall to support the operative portion of the detector within the tank and to provide access to the output of the detector outside of the vessel, said detector support means comprising
   an inner member having an inner bore adapted to receive the detector, a concave, frustoconical, seal-engaging surface, and a threaded cylindrical outer surface at one end, and
   a detector support housing having a first threaded outer surface portion to engage the threaded fitting in the tank wall, a housing inner bore at one end of the housing fastened to the other end of the outer surface of the inner member, a grommet-seating surface at the outer end of the housing inner bore, and a second threaded outer surface surrounding the grommet-seating surface;
   a grommet surrounding and supporting the detector and seated on the grommet-seating surface of the housing;
   a grommet compression nut threaded onto the second threaded outer portion of the housing with a grommet washer between the grommet and grommet compression nut;
   a first seal seated on the detector forwardly of the inner member within the tank;
   a seal compression member threadedly engaging the threaded outer surface of the inner member and compressing the first seal between the seal compression member, the frustoconical, seal-engaging surface of the inner member and the outer surface of the detector;
   a second seal seated on the inner member forwardly of the detector support housing and adjacent the interface between the inner member and the housing, said seal compression member and the threaded outer surface portion of the inner member being adapted so that the distal end of the seal compression member compresses the second seal between the distal end of the seal compression member and the detector support housing, said system thereby limiting exposure of fermentation materials to outwardly exposed surfaces of the system.

2. In a system for the preparation of biological agents including a vessel in which biological agents are prepared by fermentation and in which the fermentation process is monitored by a probe detection means, the improvement comprising probe support means adapted to fasten to the wall of a vessel and to support the probe detection means with its operative end exposed to the material being fermented within the tank and to provide access from outside the tank to the output of the probe detection means, a seal seated on the probe detection means forwardly of probe support means, said probe support means having a cylindrical threaded portion and a seal-engaging surface at its end within the tank, and a seal compression member threadedly engaging the cylindrical threaded portion of the probe support means to compress the seal against the seal-engaging surface of the probe support means and the outer surface of the probe detection means, thereby limiting the collection of fermentation material to the exposed outer surfaces of the system and permitting sterilization of the system inside of the vessel.

3. The improvement of claim 2 wherein the seal compression member includes an annular flange with a concave, frustoconical, seal-engaging surface formed in the inner surface of the annular flange and a concave, frustoconical surface formed in the outer surface of the annular flange to substantially eliminate an annular recess between the outer surface of the probe and the annular flange of the seal compression member.

4. A system for the preparation of biological agents, comprising a vessel for the biological agents;

an opening in the vessel wall;

a detector to monitor the process in the vessel;

detector support means in the opening in the vessel wall to support the operative portion of the detector within the vessel and provide access to the output of the detector outside of the vessel, said detector support means having an inner bore adapted to receive, engage and support the detector and a concave, seal-engaging surface and a threaded outer surface at its end within the vessel, and further having an outer portion adapted to engage the opening in the vessel wall;

a seal seated on the detector forwardly of the threaded outer surface of detector support means within the vessel;

a seal compression member threadedly engaging the threaded outer surface of the detector support means and compressing the seal between the seal compression member, the seal-engaging surface of the detector support means and the outer surface of the detector, said system thereby limiting biological agents to outwardly exposed surfaces of the system.

5. The system of claim 4 including a second seal seated on the detector support means rearwardly of its threaded outer surface within the vessel, said seal compression member and the threaded outer surface of the detector support means being adapted so that the distal end of the seal compression member compresses the second seal between the detector support means and the distal end of the seal compression member as it compresses the seal seated on the detector.

6. The system of claim 4 or claim 5 wherein the seal-engaging surface of the dectector support means is a concave, frustoconical surface cut at an angle of about 45° with respect to the central axis of the detector support means, the seal compression member has an annular flange at the end opposite its threaded portion, the inner surface of the annular flange has an inner frustoconical, seal-engaging surface cut at an angle of about 45° with respect to its central axis and the outer surface of the annular flange has a concave, frustoconical outer surface cut at about 30° with respect to its central axis that intersects its inner frustoconical, seal-engaging surface.

7. A detector support for systems for the preparation of biological agents, comprising detector support means adapted to engage the wall of a fermentation vessel to support the operative portion of a probe detector within the vessel and to provide access to the output of the detector outside of the vessel;

said detector support means having an inner bore adapted to receive a probe detector and a concave, seal-engaging surface and a threaded outer surface at its end to be inserted within the vessel, and further having a portion adapted to engage the vessel wall, and a surface adapted to permit engagement and support of a probe detector; and a seal compression member adapted to threadedly engage the threaded outer surface of the detector support means and having a surface adapted to cooperate with the seal-engaging surface of the detector support means and to compress a seal between the seal compression member and the seal-engaging surface of the detector support means and urge the seal against the outer surface of a probe detector to limit fermentation materials to outwardly exposed surfaces of the system.

8. The detector support of claim 7 wherein the detector support means is adapted to receive a second seal rearwardly of the threaded outer surface within the vessel, said seal compression member and the threaded outer surface of the detector support means being of such length that the distal end of the seal compression member can compress the second seal between the detector support means and the distal end of the seal compression member.

9. The detector support of claim 7 or claim 8 wherein the seal-engaging surface of the detector support means is a concave, frustoconical surface cut at an angle of about 45° with respect to the central axis of the detector support means, the seal compression member has an annular flange at the end opposite its threaded portion, the inner surface of the annular flange has an inner frustoconical, seal-engaging surface cut at an angle of about 45° with respect to its central axis and the outer surface of the annular flange has a concave, frustoconical outer surface cut at about 30° with respect to its central axis that intersects its inner frustoconical, seal-engaging surface.

* * * * *